US006702776B2

(12) United States Patent
Quinn

(10) Patent No.: US 6,702,776 B2
(45) Date of Patent: Mar. 9, 2004

(54) BLOOD VESSEL CATHETER

(75) Inventor: David G. Quinn, Grayslake, IL (US)

(73) Assignee: Radius International Limited Partnership, Grayslake, IL (US)

( * ) Notice: Subject to any disclaimer, the term of this patent is extended or adjusted under 35 U.S.C. 154(b) by 426 days.

(21) Appl. No.: 09/759,582

(22) Filed: Jan. 11, 2001

(65) Prior Publication Data

US 2001/0018576 A1 Aug. 30, 2001

Related U.S. Application Data

(63) Continuation-in-part of application No. PCT/US00/32000, filed on Nov. 21, 2000, which is a continuation-in-part of application No. 09/651,763, filed on Aug. 30, 2000, now Pat. No. 6,517,529, and a continuation-in-part of application No. 09/651,455, filed on Aug. 30, 2000, now Pat. No. 6,540,714, and a continuation-in-part of application No. 09/448,130, filed on Nov. 24, 1999, now abandoned.

(51) Int. Cl.[7] .................................................. A61M 3/00
(52) U.S. Cl. ........................ 604/43; 604/6.16; 604/524; 138/177
(58) Field of Search ........................ 604/43, 6.16, 524, 604/541, 264, 266, 270, 523, 528, 4.01, 525; 138/118, 172, 177, DIG. 11, 178, 92

(56) References Cited

U.S. PATENT DOCUMENTS

| 1,879,249 | A | 9/1932 | Honsaker |
|---|---|---|---|
| 2,116,083 | A | 5/1938 | Rusch |
| 3,384,089 | A | 5/1968 | Shriner |
| 3,589,368 | A | 6/1971 | Jackson et al. |
| 4,037,599 | A | 7/1977 | Raulerson |
| 4,134,402 | A | 1/1979 | Mahurkar |
| 4,270,542 | A | 6/1981 | Plumley |
| 4,311,140 | A | 1/1982 | Bridgman |
| 4,368,737 | A | 1/1983 | Ash |
| 4,381,011 | A | 4/1983 | Somers, 3rd |
| 4,445,897 | A | 5/1984 | Ekbladh et al. |
| 4,490,143 | A | * 12/1984 | Quinn et al. ................. 604/270 |
| 4,498,902 | A | 2/1985 | Ash et al. |
| 4,529,399 | A | 7/1985 | Groshong et al. |
| 4,549,879 | A | 10/1985 | Groshong et al. |
| 4,559,039 | A | 12/1985 | Ash et al. |
| 4,568,329 | A | 2/1986 | Mahurkar |
| 4,583,968 | A | 4/1986 | Mahurkar |
| 4,623,327 | A | 11/1986 | Mahurkar |
| 4,639,252 | A | 1/1987 | Kelly et al. |
| 4,671,796 | A | 6/1987 | Groshong et al. |
| 4,692,141 | A | 9/1987 | Mahurkar |
| 4,692,153 | A | 9/1987 | Berlin et al. |
| 4,701,166 | A | 10/1987 | Groshong et al. |
| 4,770,652 | A | 9/1988 | Mahurkar |
| 4,772,266 | A | 9/1988 | Groshong |
| 4,781,678 | A | 11/1988 | de Couët et al. |

(List continued on next page.)

Primary Examiner—Brian L. Casler
Assistant Examiner—Jeremy Thissell
(74) Attorney, Agent, or Firm—Brinks Hofer Gilson & Lione

(57) ABSTRACT

A catheter including a catheter tube and a bolus tip, the bolus having a radially extending main side port. In one embodiment the catheter also has second and third side ports axially spaced from said main side port. The second and third side ports are each axially elongated, with an edge which is semi-circular in cross-section. The second side port is displaced 180° from the main side port. The third side port is axially aligned with the main port. The catheter is thickened in a dimple opposite each of the second and third side ports. Another catheter embodiment specifically for hemodialysis includes a dual lumen tube with a bolus at its distal end. A main venous port is formed in one side of the bolus adjacent the bullet nose of the bolus. Variations of this embodiment utilize a bolus with a 13.5 French tube connector section and a 10 French nose section, with the venous port formed in the nose section.

22 Claims, 10 Drawing Sheets

U.S. PATENT DOCUMENTS

| | | |
|---|---|---|
| 4,808,155 A | 2/1989 | Mahurkar |
| 4,842,582 A | 6/1989 | Mahurkar |
| 4,895,561 A | 1/1990 | Mahurkar |
| 4,898,669 A | 2/1990 | Tesio |
| 5,053,004 A | 10/1991 | Markel et al. |
| 5,197,951 A | 3/1993 | Mahurkar |
| 5,221,255 A | 6/1993 | Mahurkar et al. |
| 5,221,256 A | 6/1993 | Mahurkar |
| 5,322,519 A | 6/1994 | Ash |
| 5,336,177 A | 8/1994 | Marcus |
| 5,336,178 A * | 8/1994 | Kaplan et al. .............. 604/509 |
| 5,374,245 A | 12/1994 | Mahurkar |
| 5,378,230 A | 1/1995 | Mahurkar |
| 5,451,216 A | 9/1995 | Quinn |
| 5,486,159 A | 1/1996 | Mahurkar |
| 5,571,093 A | 11/1996 | Cruz et al. |
| 5,599,322 A | 2/1997 | Quinn |
| 5,607,405 A | 3/1997 | Decker et al. |
| 5,624,413 A | 4/1997 | Markel et al. |
| 5,685,836 A | 11/1997 | DiPerna et al. |
| 5,776,111 A | 7/1998 | Tesio |
| 5,947,953 A | 9/1999 | Ash et al. |
| 5,984,913 A | 11/1999 | Kritzinger et al. |
| 6,461,321 B1 * | 10/2002 | Quinn ........................ 604/43 |
| 6,517,529 B1 * | 2/2003 | Quinn ........................ 604/528 |
| 6,540,714 B1 * | 4/2003 | Quinn ........................ 604/43 |
| 2002/0026156 A1 * | 2/2002 | Quinn ........................ 604/264 |
| 2003/0032918 A1 * | 2/2003 | Quinn ........................ 604/43 |

* cited by examiner

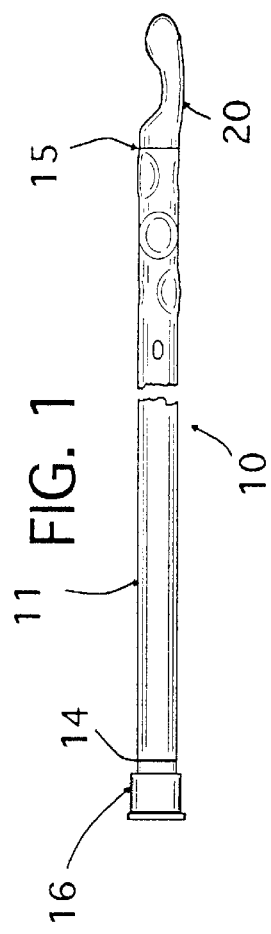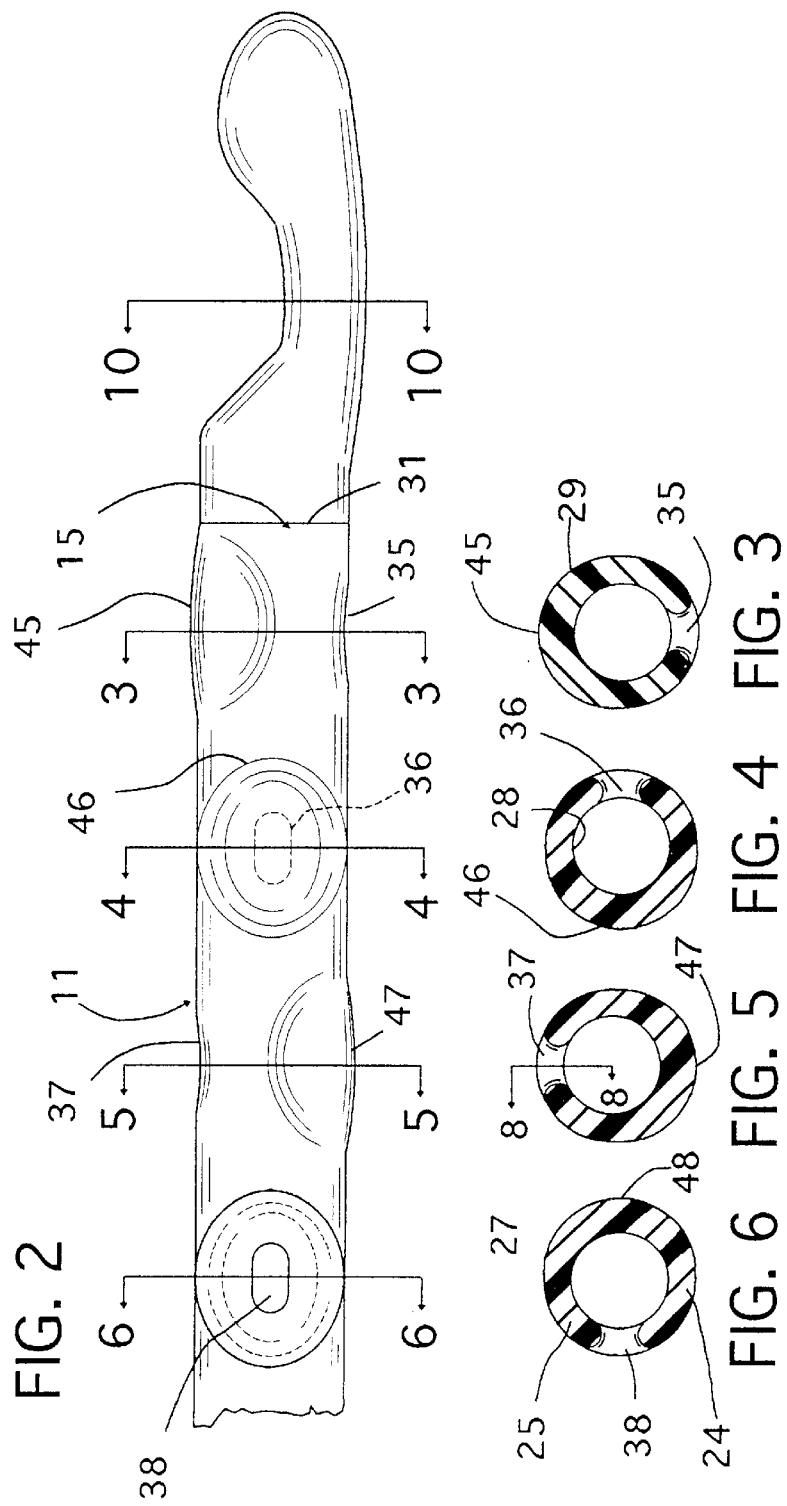

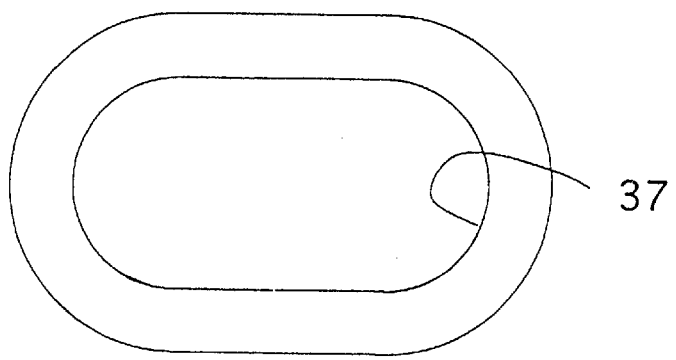
FIG. 7
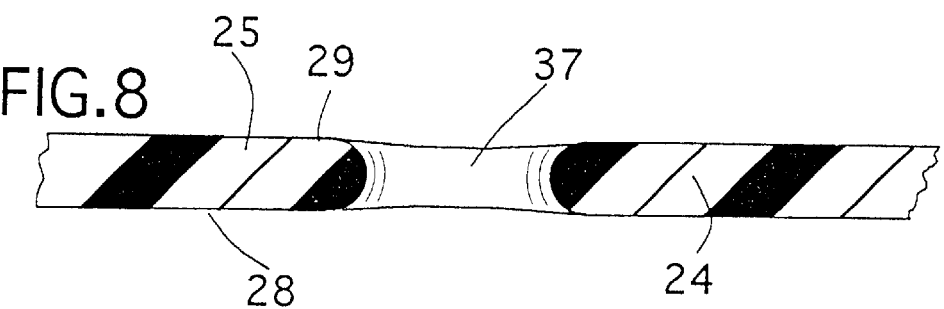
FIG. 8
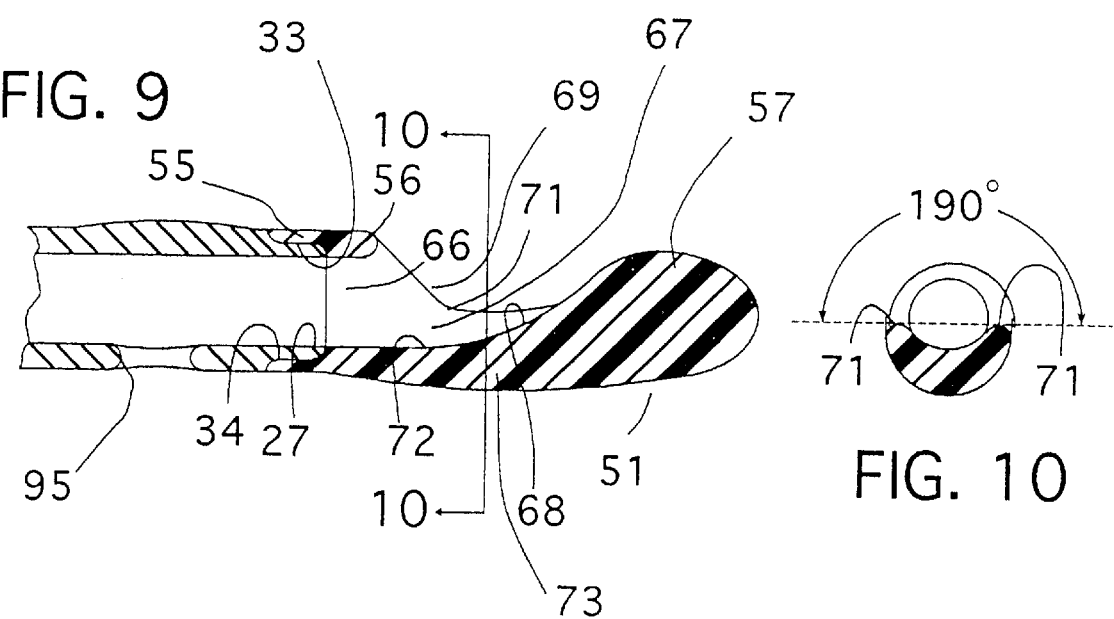
FIG. 9
FIG. 10

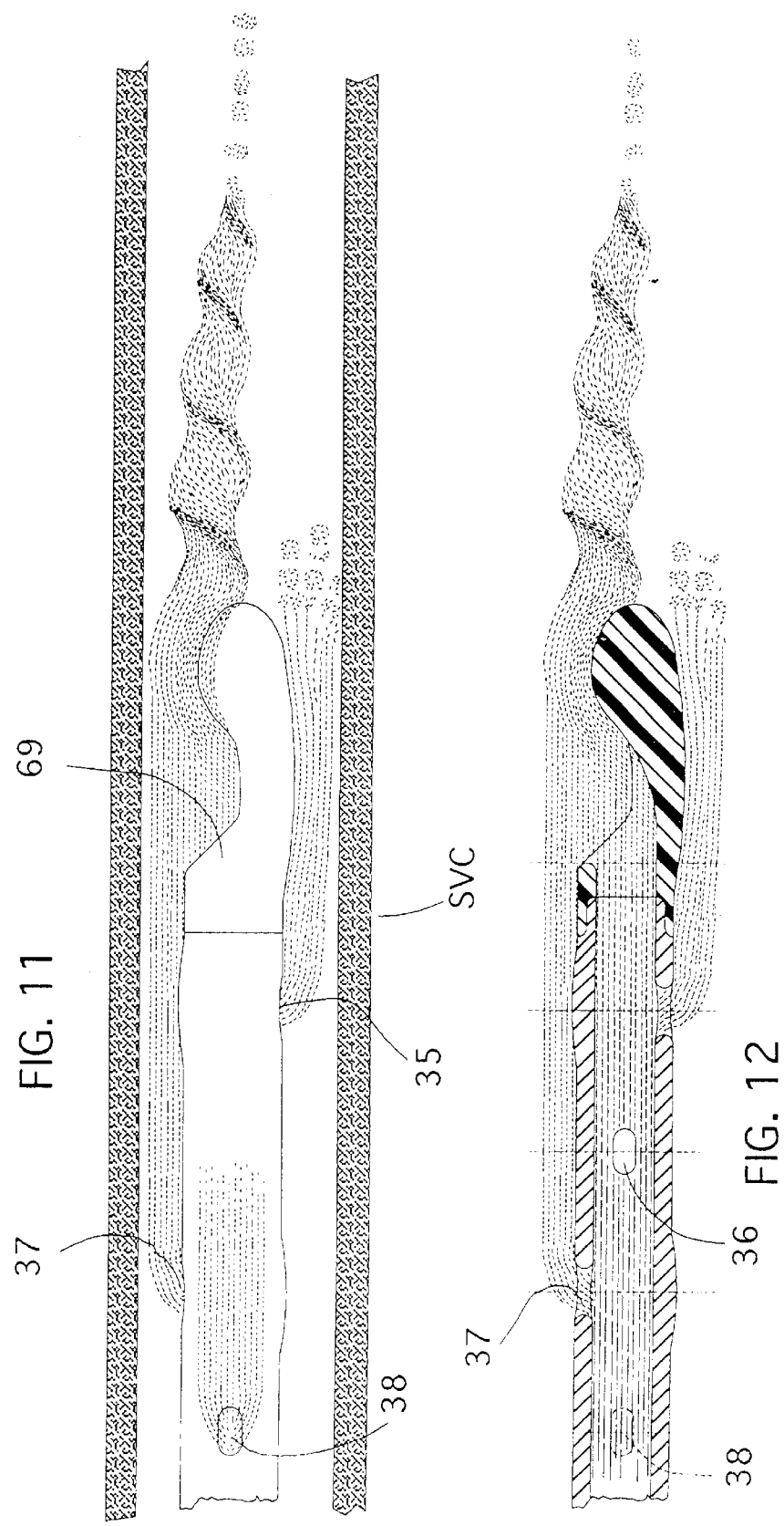

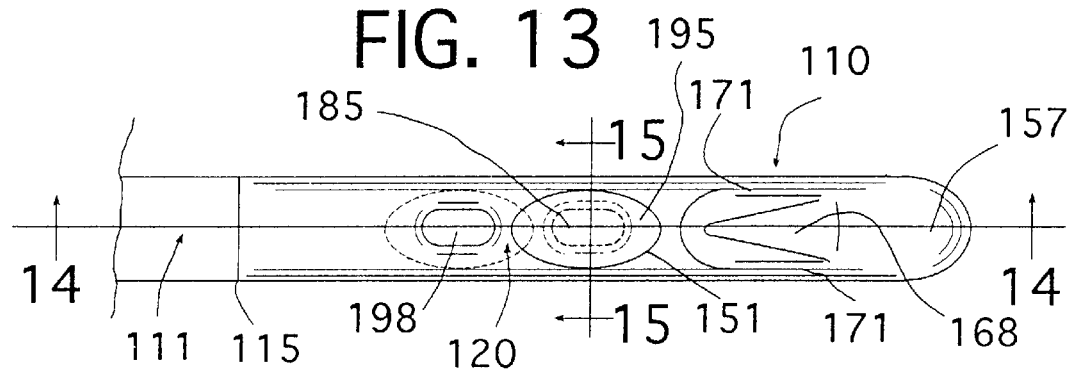
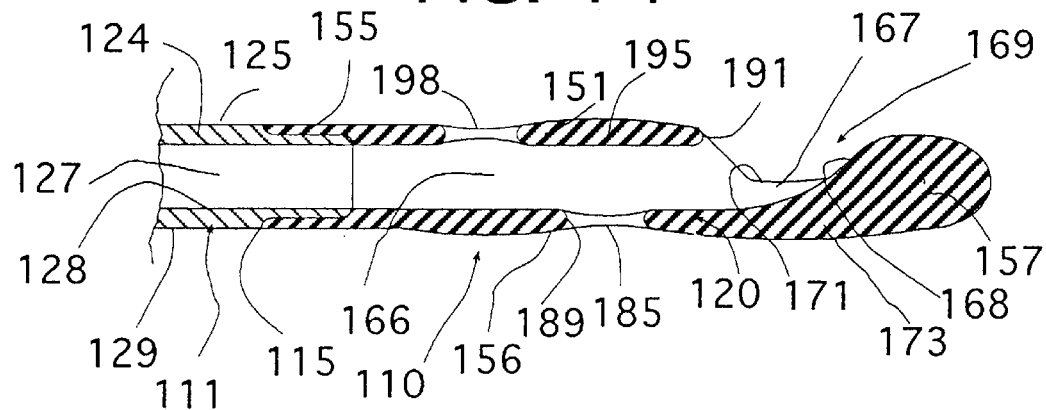
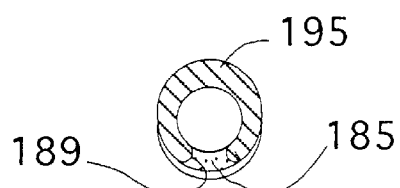
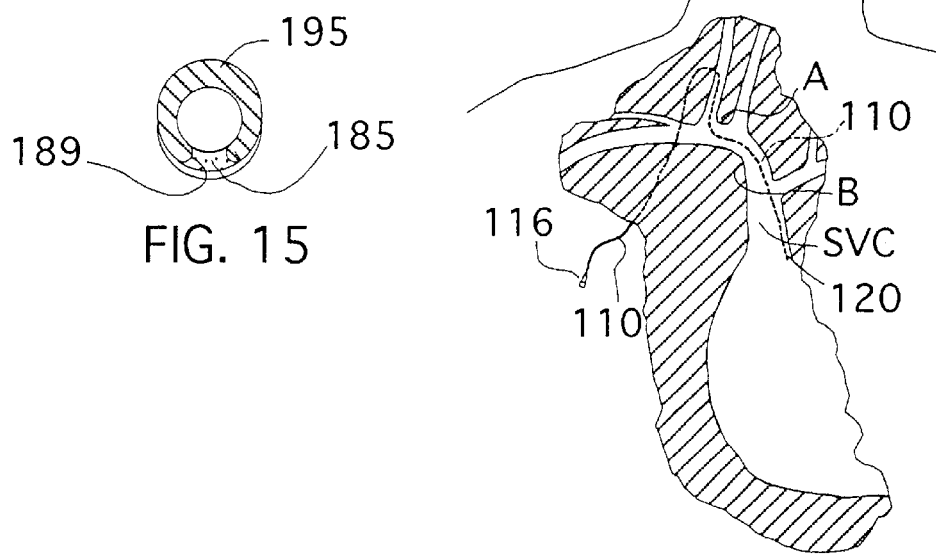

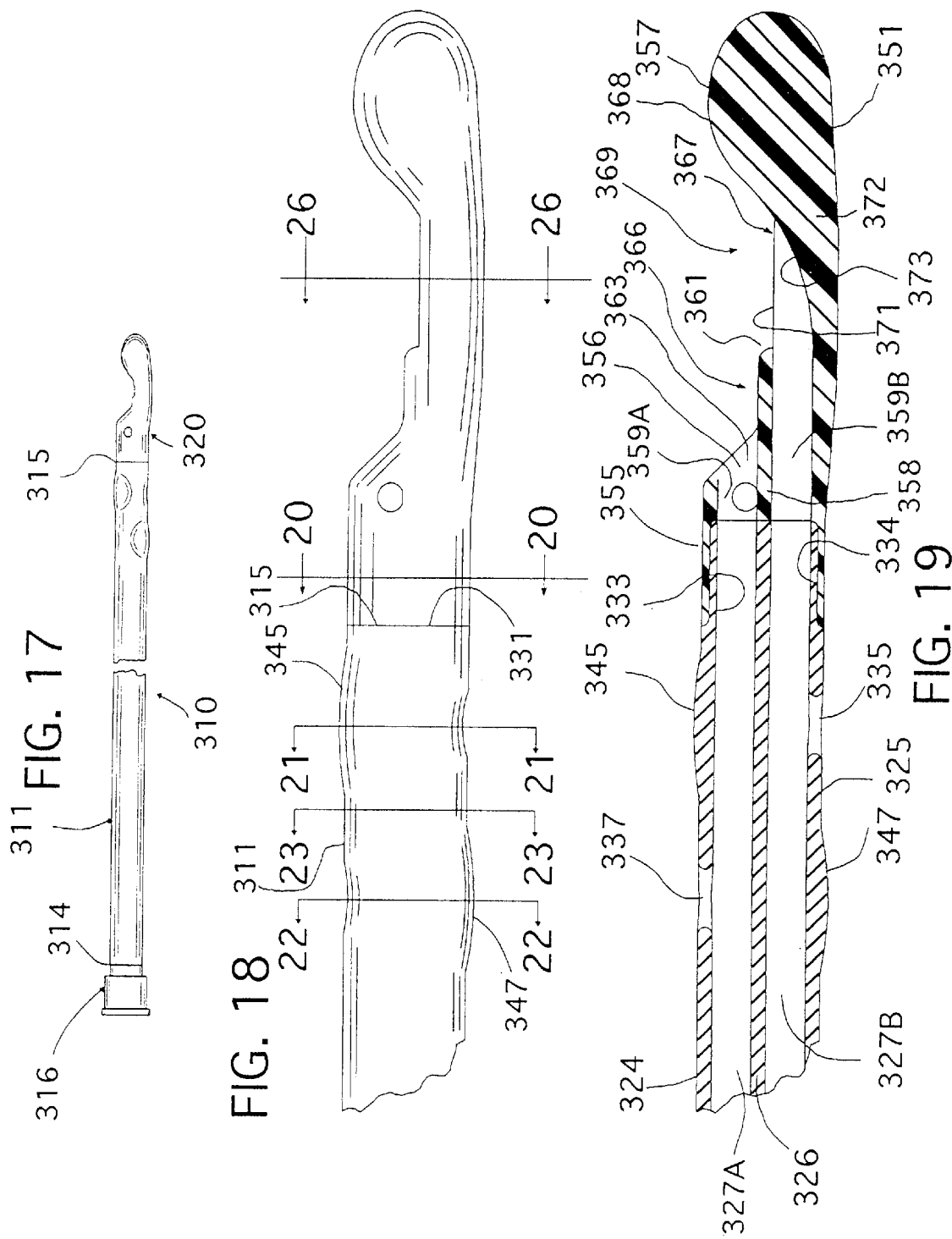

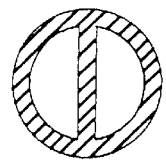
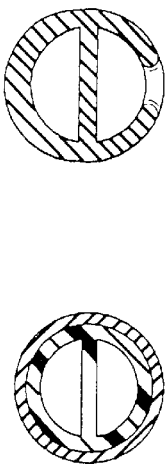
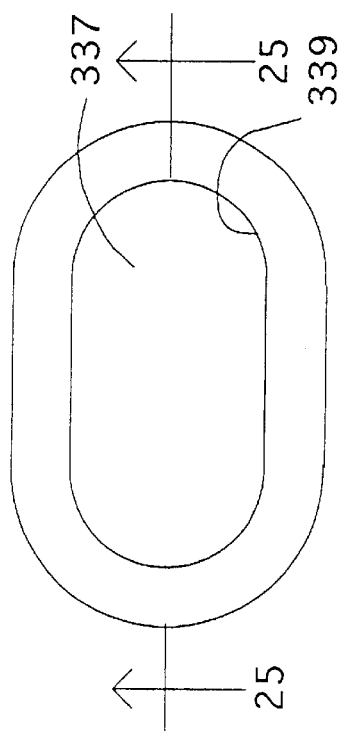
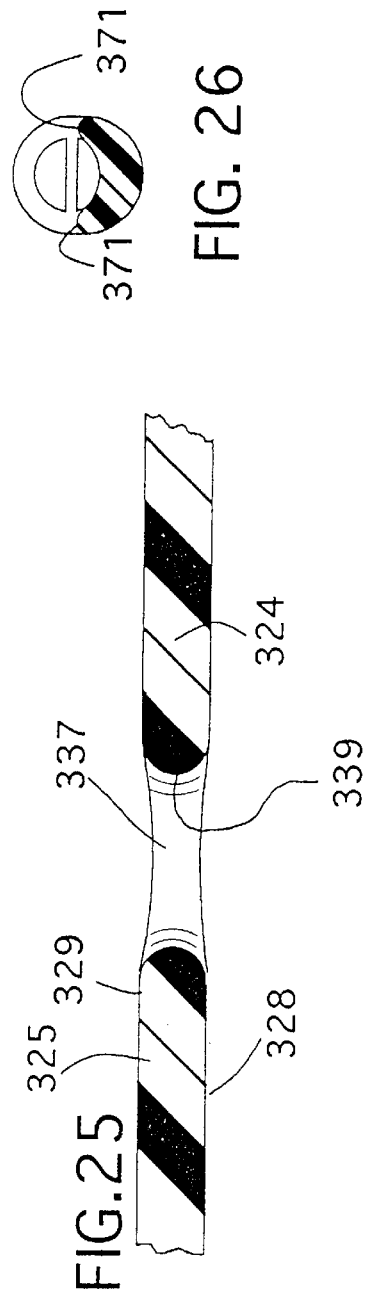

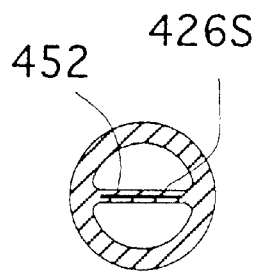
FIG. 30
FIG. 34
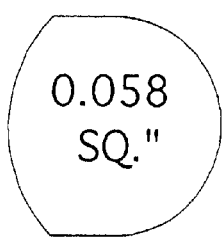
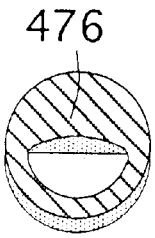
FIG. 32
FIG. 33
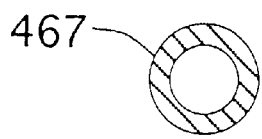
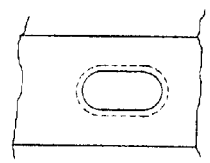
FIG. 35
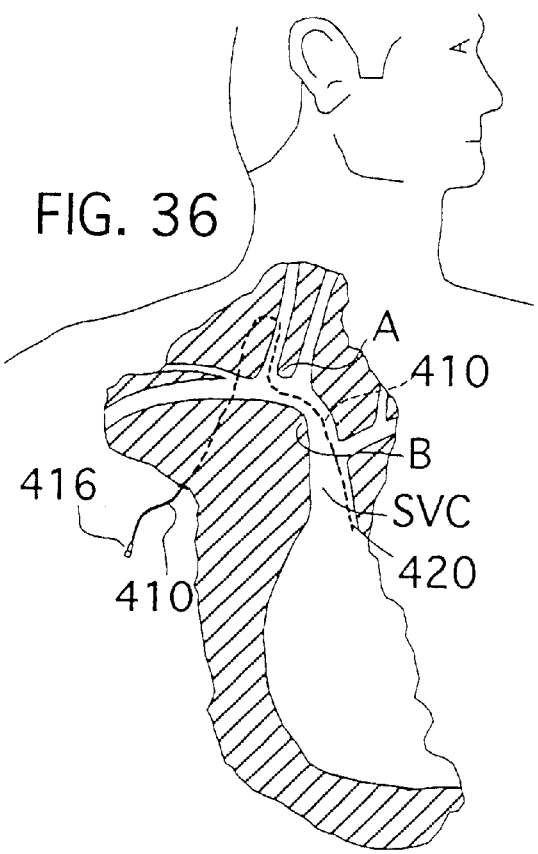
FIG. 36
FIG. 31
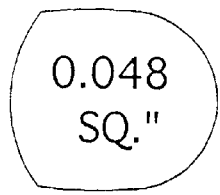

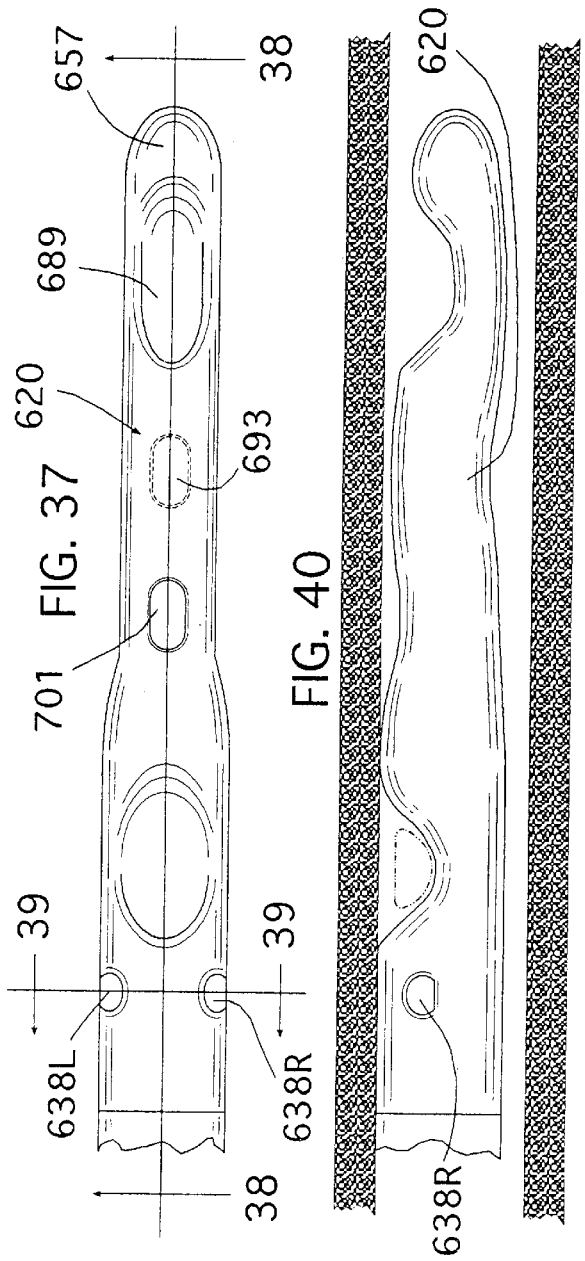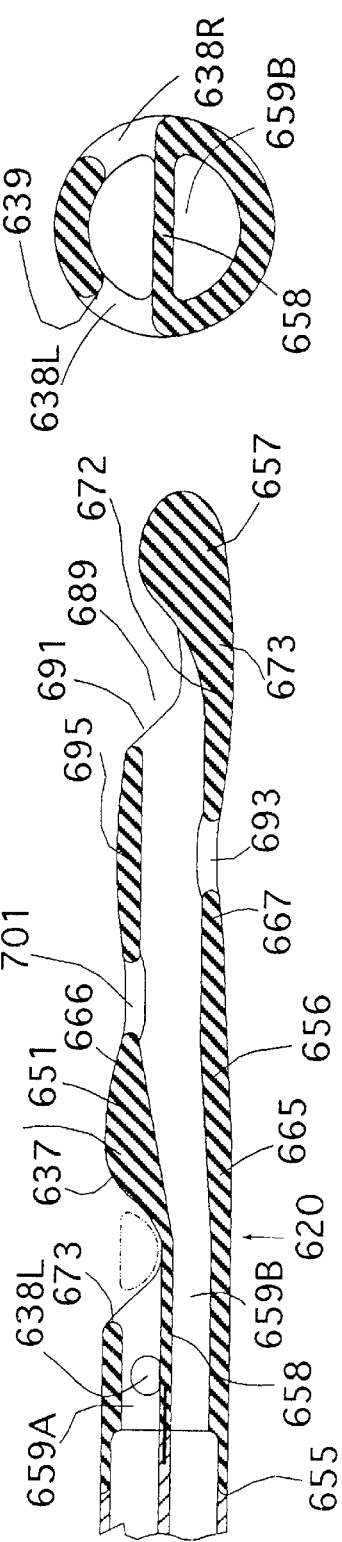

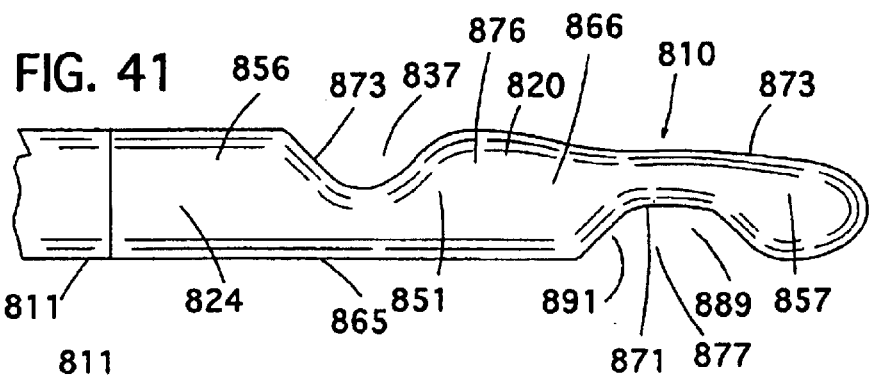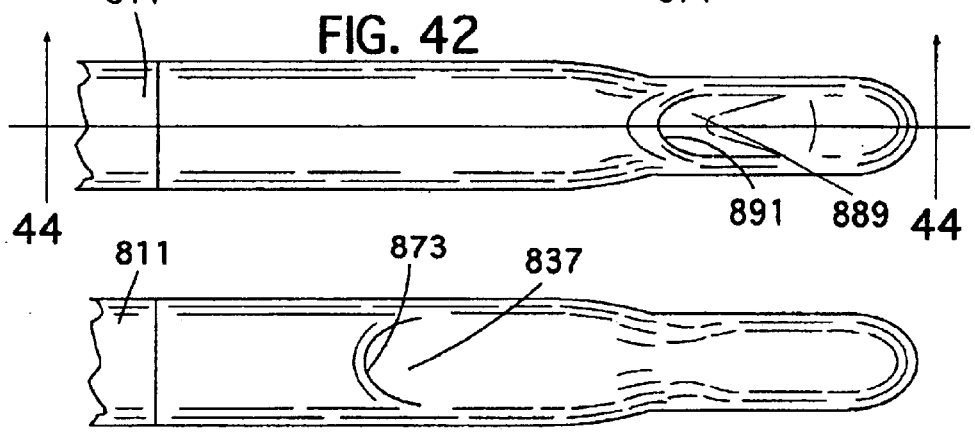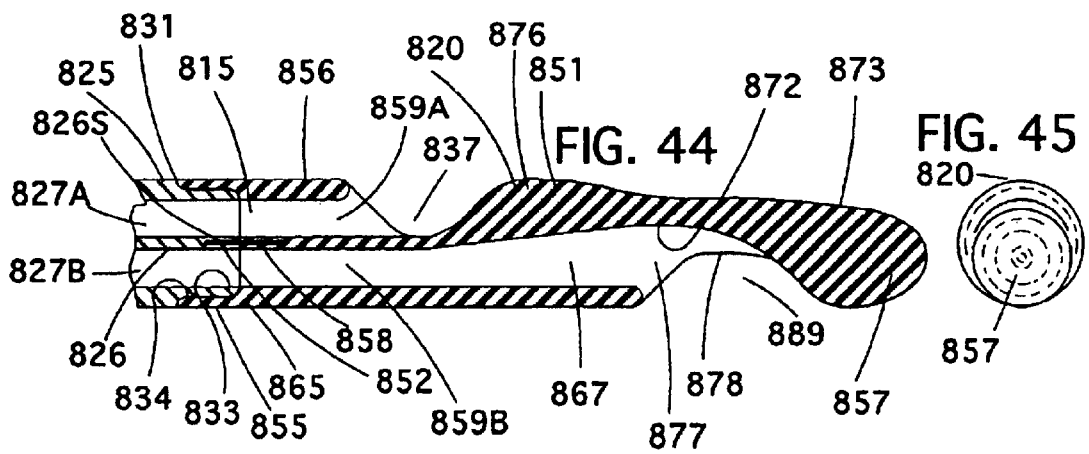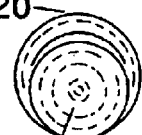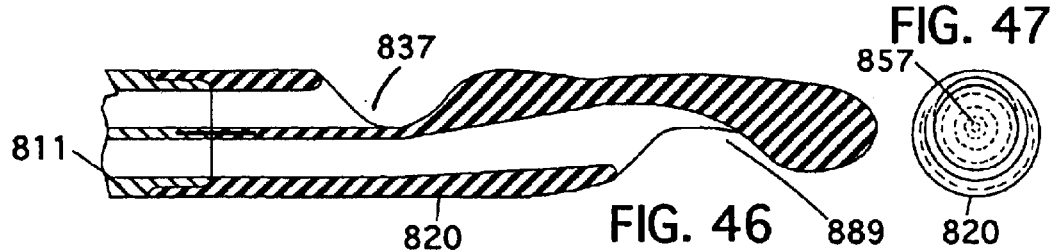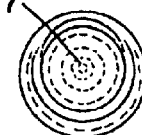

BLOOD VESSEL CATHETER

RELATED APPLICATIONS

This application is a continuation in-part of PCT application No. PCT/US00/32000 filed Nov. 21, 2000, which is continuation-in-part of, and claims priority from, U.S. application Ser. No. 09/448,130 filed Nov. 24, 1999 (now abandoned), U.S. application Ser. No. 09/651,455 filed Aug. 30, 2000 now U.S. Pat. No. 6,540,714 and U.S. application Ser. No. 09/651,763 filed Aug. 30, 2000 now U.S. Pat. No. 6,517,529.

FIELD OF THE INVENTION

This invention relates in general to medical catheters and, more particularly, to blood vessel catheters. In one aspect of the invention it relates to hemodialysis catheters.

BACKGROUND OF THE INVENTION

Blood vessel catheters are normally either venous catheters or arterial catheters. Venous catheters, in turn, usually come in several forms. The simplest are short peripheral catheters. Next come midline catheters, central venous catheters and port catheters. A hemodialysis catheter is one form of central venous catheter and is normally placed in the superior vena cava. The present invention may find application in each of the aforementioned venous catheters. However, it finds particularly advantageous application in hemodialysis catheters.

Hemodialysis, as practiced today, normally employs one of two types of catheter to remove blood from the patient for processing and return processed blood to the patient. Most commonly, a catheter tube containing two lumens is used, each lumen having a semi-cylindrical configuration. This is frequently referred to as a dual lumen catheter. Alternatively, two separate tubes, each with a full cylindrical configuration, may be used to remove blood for dialysis and return the processed blood.

Hemodialysis membranes are now able to process blood at over 500 ml of flow per minute. Even higher processing rates are foreseeable. However, problems occur with both the line introducing purified blood back into the vein (the venous line) and the line removing blood for purification (the arterial line) at flow rates above 300 ml per minute. A high flow rate from the venous line can cause whipping or "firehosing" of the tip in the vein with consequent damage to the vein lining. A corresponding high flow rate into the arterial line causes the port to be sucked into the vein wall, resulting in occlusion. It should be understood, of course, that both lines normally access the superior vena cava and the designations are used for differentiation purposes.

Speed of flow through a catheter lumen, whether it be in a single lumen or a dual lumen catheter, is controlled by a number of factors including the smoothness of the wall surface, the internal diameter or cross-sectional area of the tube lumen, and the length of the tube lumen. The most important factor is the cross-sectional area of the tube lumen. The force or speed of the fluid flow in a tube lumen for a given cross-sectional area is controlled by the external pumping force, of course. This is a positive pressure pushing processed blood through the venous lumen and a negative (suction) pressure pulling unprocessed blood through the arterial lumen.

Problems encountered in providing for a high flow rate through a catheter are magnified in a dual lumen catheter construction. Because each of the lumens in a dual lumen catheter has a D-shape, it has been assumed that flow rates are limited. Furthermore, such dual lumen catheters are, to a great extent, catheters with a main port which opens at the end of a lumen substantially on the axis of the lumen. Thus, firehosing frequently results. There are dual lumen catheters which utilize side ports for both outflow and inflow. An example is the catheter disclosed in the Cruz et al. U.S. Pat. No. 5,571,093. However, such catheters have not been successful in solving numerous problems related to hemodialysis with dual lumen catheters, e.g., high incidences of catheter port occlusion as well as some degree of fire-hosing still occurs.

A flow balance between the venous and arterial lines is also of obvious importance. Occlusion of the arterial line is a very common limiting factor in hemodialysis. While the venous line tends to remain clear and open, because the direction of flow forces tube ports away from the vein wall, in the arterial line this high flow tends to pull the port against the vein wall, thereby sucking the wall into the port and occluding it. Andersen et al. U.S. Pat. No. 4,594,074, Quinn U.S. Pat. No. 5,451,216, Quinn U.S. Pat. No. 5,810,787, Quinn U.S. Pat. No. 5,599,322 and Quinn U.S. Pat. No. 5,571,093 all discuss the need for improved aspiration in catheters generally.

Additionally, some key problems face dialysis clinicians using dual lumen central venous catheters or catheters placed via the jugular route. Clinicians routinely face a situation where either the venous or the arterial lines fail to function during dialysis, or when the patent is first connected to the dialysis machine. The dialysis center clinician must find a way to make the system work as he or she does not have the option of immediately changing the catheter. Failure is most often on the arterial or pulling side, where the catheter port is sucked against the vessel wall. Occlusion can also be caused by a combination of clots and the proximity of the vessel wall. The problem is frequently addressed by reversing the lines, by flushing the lines with saline and/or by repositioning the patient so that gravity can help move the catheter tip way from the vessel wall. Insofar as reversing the lines is concerned, although it can be very effective, it also may result in ineffective dialysis because venous (dialyzed) and arterial blood tend to mix more easily when venous blood is then being directed at the arterial port instead of away from it.

SUMMARY OF THE INVENTION

An object of the present invention is to provide an improved blood vessel catheter.

Another object is to provide a blood vessel catheter which substantially reduces the opportunity for occlusion to occur during outflow.

Another object is to provide an improved hemodialysis catheter which is capable of delivering processed blood to the patient at high flow rates without harmful firehosing or whipping of the catheter tip.

A further object is to provide a hemodialysis catheter which is capable of returning processed blood to the patient at flow rates of 500 ml or greater without traumatizing the patients blood vessel.

Yet a further object is to provide a hemodialysis catheter which permits high flow rates while minimizing trauma and potential red cell and platelet damage so as to avoid clotting.

Yet another object is to provide a hemodialysis catheter which permits substantially increased venous flow rates while reducing output force and increasing the diffusion rate.

Another object is to provide a dual lumen hemodialysis catheter which permits flow rates higher than the latest separate lumen catheters without harmful firehosing of the catheter tip.

Yet another object is to provide a dual lumen hemodialysis catheter which permits high flow rates while minimizing trauma and potential red cell and platlet damage so as to substantially avoid clotting.

A further object is to provide a dual lumen hemodialysis catheter which substantially reduces the incidence of arterial port occlusion.

Still a further object is to provide a dual lumen hemodialysis catheter in which flow can be reversed without significant mixing of venous and arterial blood.

Yet a further object is to provide new and improved bolus tips for dual lumen, hemodialysis catheters.

The foregoing and other objects are realized in accord with the present invention by providing a first embodiment of blood vessel catheter which combines a single lumen catheter tube and a bolus tip. The bolus tip has a bullet nose and a main side port. The catheter has at least one additional radially extending side port displaced axially from the main side port. The additional port or ports are elongated axially of the catheter so as to have a race-track shaped edge. The edge is semi-circular in cross-section.

In one form of the first embodiment, the catheter tube has an elongated cylindrical body, fabricated of thermoplastic material such as polyurethane, or thermoset material such as silicone rubber. An axial passageway or lumen extends the length of the cylindrical body, from a proximal to a distal end. The cylindrical wall which defines the lumen has an axially and circumferentially spaced series of radially extending ports formed in it adjacent the distal end. Each port is elongated axially of the body so as to have a race-track shaped edge. The race-track shaped edge is semi-circular in cross-section around its entire length.

Directly opposite each port in the body of the tube, the body wall is thickened in an oval pattern to form a longitudinally elongated dimple. The dimple forms a stiffening arch in the tube wall. The arch serves to prevent the tube from buckling at the port.

The distal end of the tube has a bolus tip. The bolus tip is a separate element. It is molded of the same resilient plastic. The tip may be glued or welded to the distal end of the tube. It may also be insert molded on the tube.

The bolus tip has a tube connector section adjacent the distal end of the tube, a bullet nose section and a passage section between the tube connector section and the bullet nose section. The passage section of the bolus tip has an axial passage in it adjacent the connector section and a radial passage adjacent the nose section. The axial passage is in fluid communication with the tube lumen. The radial passage leads to a main port extending radially through the side of the bolus. The main port extends circumferentially around slightly more than 180° of the bolus, i.e., about 190°.

In another form of the first embodiment, the passage section of the bolus is extended and a second port is formed in the side of this passage section. The second port is displaced 180° around the axis of the bolus from the main port in the bolus. Directly opposite the second port, the passage section wall is thickened to form a longitudinally elongated dimple. A third port axially aligned with the main port and 180° and displaced from the second port may also be used. The passage section wall is also thickened to form a longitudinally elongated dimple opposite the third port.

The dimple opposite the second port stiffens the bolus at the second port and tends to hold the main port away from the vein wall. As such, it aids in preventing occlusion of the main port and, also, protects the vein wall from abrasion by the edge of the main port.

In a conventional single lumen hemodialysis catheter, for example, substantially the full pumping force is directed axially out of the end of the catheter because of its end port orientation and the size and shape of any side ports employed. Little flow is directed through such side ports. The aforedescribed embodiment provides a side port or ports which allow higher flow rates. This redirection of flow through a longitudinally elongated side port or ports separated from the main side port in the bolus reduces the speed or force of flow from each port. This reduction in force results in better diffusion and protects against whipping. In addition, the port configurations are smoother and have no sharp edges to damage blood cells. During arterially or inflow to such a catheter, clogging and occlusion due to "vein wall sucking" is substantially avoided.

A second embodiment of hemodialysis catheter includes a dual lumen catheter tube and bolus. The bolus has a main outflow or venous port. At least one intake or arterial port extends radially through the bolus or the tube.

In one form of the second embodiment, the arterial and the venous lumens open through a radially extending main venous port and a main intake or arterial port which are immediately adjacent each other on one side of the bolus next to the bullet nose in the bolus. The venous lumen also opens through a second outflow port formed in the tube adjacent the bolus and circumferentially displaced 180° around the axis of the catheter tube from the main venous port. Directly opposite this second venous port, which is longitudinally elongated, the tube body wall is thickened in an oval pattern to form a longitudinally elongated dimple. The dimple forms a stiffening arch in the tube wall and prevents buckling of the tube at the second venous or outflow port.

In another form of the second embodiment, the venous and arterial lumens open through radially extending, axially displaced main outflow and intake ports on the same side of the catheter bolus. A main outflow port for the venous lumen port is formed radially in the bolus adjacent its bullet nose. A second outflow port for the venous lumen is formed radially in the bolus, circumferentially removed 180° from the main port and displaced axially from the main port. A third outflow port is formed radially in the bolus, axially aligned with the main outflow port and axially displaced from both the main and second outflow ports. A main inflow or arterial port is formed radially in the bolus at a point axially displaced in the bolus from the outflow ports.

In this form of the invention, directly opposite each of the second and third outflow ports and the main intake port the tube body wall is thickened in an oval pattern to form a longitudinally elongated dimple. Each dimple forms a stiffening arch in the bolus and prevents buckling of the bolus at the corresponding ports.

In this form of the invention also, the dual lumen tube is preferably a 13.5 French tube, giving it a nominal O.D. of 0.180 inches. The bolus tip, on the other hand, is 10 French size, i.e., it has a nominal O.D. of 0.136 inches. The bolus tapers from the 13.5 French size to the 10 French size between the second and third ports. As such, the inflow lumen has a D-shape until it reaches a tapered middle of the bolus, whereupon it transitions to a circular cross-section. At the same time the cross-sectional area of the lumen increases from about 0.005 in$^2$ to about 0.006 in$^2$. This form of bolus is 1.62 inches long.

In a variation of this form of bolus, the bolus body is shorter, being only 1.46 inches long. This is achieved by shortening the transition sub-section of the bolus body (between the 13.5 French and 10 French diameters) and moving the second and third venous ports closer together. The stiffening arch beneath the third venous port is eliminated and the transition section thickness serves the same purpose. The shorter bolus body is even less likely to kink under bending stress.

In another variation of this form of the invention, the venous and arterial ports are displaced 180° from each other about the axis of the bolus. As a result, even when flow is reversed from its normal pattern, no significant mixing of venous and arterial blood flow results. The outflow diversion and dispersion characteristics of the venous and arterial ports arranged in this way assures that venous flow from the upstream port (normally arterial) will flow past the (then) arterial port without any significant mixing taking place.

BRIEF DESCRIPTION OF THE DRAWINGS

The invention, including its construction and method of operation, is illustrated more or less diagrammatically in the drawings, in which:

FIG. 1 is a side elevational view of one form of a first embodiment of hemodialysis catheter comprising features of the present invention;

FIG. 2 is an enlarged side elevational view of the tip end of the catheter of FIG. 1;

FIG. 3 is a sectional view taken along line 3—3 of FIG. 2;

FIG. 4 is a sectional view taken along line 4—4 of FIG. 2;

FIG. 5 is a sectional view taken along line 5—5 of FIG. 2;

FIG. 6 is a sectional view taken along line 6—6 of FIG. 2;

FIG. 7 is an enlarged plan view of one of the catheter tube ports in the catheter;

FIG. 8 is a sectional view taken along line 8—8 of FIG. 5;

FIG. 9 is a longitudinal sectional view through the bolus end of the catheter seen in FIGS. 1 and 2;

FIG. 10 is a sectional view taken along line 10—10 of FIG. 2;

FIG. 11 is an enlarged side elevational view of the catheter of FIG. 2, showing the catheter of the invention in position in a patient's blood vessel and the processed blood flow pattern created;

FIG. 12 is a longitudinal sectional view through the catheter seen in FIG. 11;

FIG. 13 is a top plan view of another form of the first embodiment of hemodialysis catheter comprising features of the invention, with parts removed;

FIG. 14 is a sectional view taken along line 14—14 of FIG. 13;

FIG. 15 is a sectional view taken along line 15—15 of FIG. 13;

FIG. 16 is an illustration of portions of a patient's anatomy, showing placement of a catheter in the patient's superior vena cava;

FIG. 17 is a side elevational view of one form of a second embodiment of the hemodialysis catheter comprising features of the present invention;

FIG. 18 is an enlarged side elevational view of the tip end of the catheter in FIG. 17;

FIG. 19 is a longitudinal sectional view taken through the catheter seen in FIG. 18;

FIG. 20 is a sectional view taken along line 20—20 of FIG. 18;

FIG. 21 is a sectional view taken along line 21—21 of FIG. 18;

FIG. 22 is a sectional view taken along line 22—22 of FIG. 18;

FIG. 23 is a sectional view taken along line 23—23 of FIG. 18;

FIG. 24 is an enlarged plan view of one of the catheter tube ports in the catheter of FIGS. 17 and 18;

FIG. 25 is a sectional view taken along line 25—25 of FIG. 24;

FIG. 26 is a sectional view taken along line 26—26 of FIG. 18;

FIG. 30 is a sectional view taken along line 30—30 of FIG. 28;

FIG. 31 is an expanded top plan view of the outflow or venous port in the bolus end of the catheter of FIG. 27;

FIG. 32 is a sectional view taken along line 32—32 of FIG. 28;

FIG. 33 is a sectional view taken along line 33—33 of FIG. 28;

FIG. 34 is an expanded top plan view of the main intake or arterial port in the bolus end of the catheter of FIG. 28;

FIG. 35 is a bottom plan view of the second outflow or venous port in the bolus end of the catheter of FIG. 28;

FIG. 36 is a schematic illustration of a catheter installation in a patient;

FIG. 37 is a top plan view of a modified other form of second embodiment bolus;

FIG. 38 is a sectional view taken along line 38—38 of FIG. 37;

FIG. 39 is a sectional view taken along line 39—39 of FIG. 39;

FIG. 40 is a side elevational view of the catheter bolus of FIG. 37 in place in a vein;

FIG. 41 is a side elevational view of yet another form of second embodiment bolus;

FIG. 42 is a bottom plan view of the bolus seen in FIG. 41;

FIG. 43 is a top plan view of the bolus seen in FIG. 41;

FIG. 44 is a sectional view taken along line 44—44 of FIG. 42;

FIG. 45 is a front end view of the bolus of FIGS. 41–43;

FIG. 46 is a sectional view similar to FIG. 44 showing a variation of this form of bolus; and FIG. 47 is a front end view of the bolus seen sectioned in FIG. 46.

DESCRIPTION OF THE PREFERRED EMBODIMENTS

Figure 27:
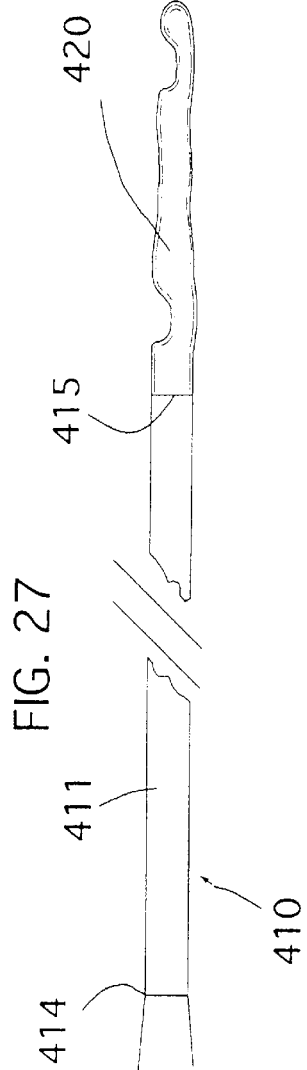
FIG. 27 is a side elevational view of another form of the second embodiment of the hemodialysis catheter comprising features of the invention, with parts removed.
Figure 28:
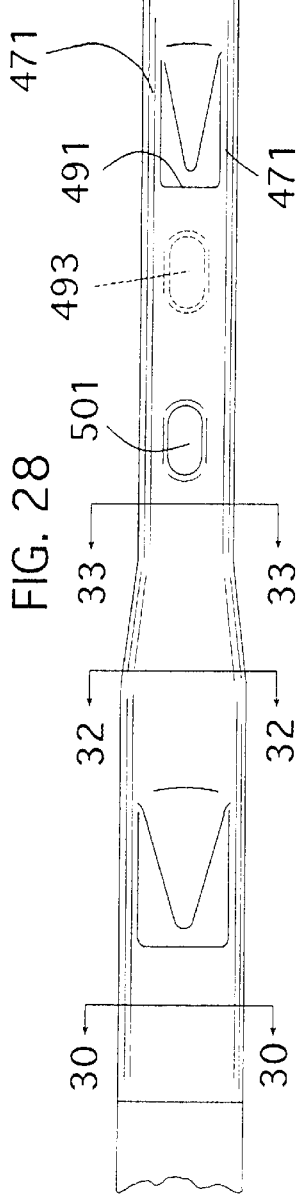
FIG. 28 is a top plan view of the bolus end of the catheter of FIG. 27.

Referring now to the drawings, and particularly to FIG. 1, a hemodialysis catheter comprising one form of a first embodiment of the invention is illustrated generally at 10. The catheter 10 comprises a cylindrical tube 11 having a proximal end 14 and a distal end 15. A bolus 20 is attached to the distal end 15.

Referring also to FIGS. 3–9, the tube 11 is a 10 French tube formed of silicone. The tube 11 comprises a tubular body 24 with a generally cylindrical wall 25 having a thickness of 0.040 inches. A lumen 27 is defined within the wall 25, extending through the body 24 along its length.

The distal end 15 of the tube 11 joins the bolus 20 at the line 31. Forward of the line 31, the tube body 24 has a necked down end 33 which is seated in a suitably formed socket 34 in the bolus 20 and glued or welded to the bolus.

The ports 35–38 are identical to each other. Accordingly, only one will be described in detail. The port 37 is formed through the tube body wall 25 during molding so as to have a race-track shape longitudinally of the tube 11. In a standard 10 French tube, the port 37 is 0.100 inches long and 0.050 inches wide.

As seen in FIGS. 5 and 8, the edge 39 of the race-track shaped port is semi-circular in cross-section, i.e., rounded along its entire length. In a 10 French tube, the wall 25 is 0.030 inches thick where the port 37 is formed, so the radius of the semi-circle is 0.015 inches. It should be understood, of course, that if tube wall 25 thickness changes because different size tubes are employed, the radius will change accordingly. In the tube 11 illustrated, the ports 35–38 are spaced longitudinally so that their centerlines, seen as the section lines 3, 4, 5 and 6 in FIG. 2, are about 0.175 inches apart.

Directly opposite each of the ports 35–38 in the tube wall 25, the wall is thickened in an oval pattern to form an elongated dimple. At its thickest, each dimple 45, 46, 47 and 48 is about 40% thicker than the rest of the tube wall 25. The dimple, best seen in FIG. 2, is centered on the corresponding port opposite it. Thus, what amounts to an oval shaped stiffening arch is formed in the tube wall 25 opposite each port, the arch being about two and one-half times as long as the corresponding port; stiffening arches 45, 46, 47 and 48 being opposite ports 35, 36, 37 and 38, respectively. The arches 45, 46, 47 and 48 stiffen the tube 11 where it otherwise might buckle because a port (35–38) opposite it has been elongated longitudinally to increase its flow capacity.

Referring specifically to FIG. 9, the bolus 20 and its connection to the terminal end 15 of the catheter tube 11 are shown in greater detail. The bolus 20 has a generally bullet-shaped body 51 fabricated from silicone. The dimensions of the body 51 vary with the size of the catheter tube 11 in use, but its outside diameter substantially equals that of the tube.

The body 51 of the bolus 20 is formed by injection molding. The bolus body 51 comprises three distinct body sections; a tube connector section 55, a flow passage section 56 and a bullet-shaped nose section 57.

The necked down end 33 of the tube body 24 is seated in the socket 34 formed in the section 55 of the bolus body 51. The end 33 is glued or welded in the socket 34. The bolus body 51 and the remainder of the tube body 24 have substantially the same outside diameter, as has been pointed out.

The lumen 27 in the tube body 24 communicates with the flow passage section 56 in the bolus body 51. The passage section 56 contains a short, axially extending passage 66 and a longer axially and radially extending passage 67 having a base 68 which curves across the axis of the body 51 to form one end of a main port 69 opening through the side of the bolus body. The main port 69 is enlarged by forming sides 71 for the passage 67 which extend down low enough so that the main port 69 extends circumferentially around about 190° of the body 51, as seen in FIG. 10. The sides 71 are inclined at a 45° angle at their trailing ends so that they do not catch on vein walls when a catheter is inserted.

Directly opposite the center of the main port 69, the floor 72 of the radial passage 67 is thickened, as at 73, to form a stiffening arch in the bolus 20. The arch 73 begins at about the end of the tube body 24, increases in thickness until it is directly under the main port 69, and then decreases in thickness to the front end of the nose section 57.

Referring now to FIG. 11, the catheter 10 is shown in place in a patient's vein V, in use as a hemodialysis catheter with processed blood being delivered through it into the vein. Processed blood flowing through the lumen 27 under pressure exits through each of the four ports 35–38 in the lumen and through the bolus main port 69. FIG. 12 shows the same catheter 10 in longitudinal section (without the blood vessel) to better illustrate flow through each port 35–38 and 69.

As will be seen, the lumen second port 35, which is immediately adjacent the bolus 20, is displaced 180° around the axis of the lumen 27 and bolus 20 from the bolus main port 69. As a result, the reaction forces created by the exiting processed blood and acting on the catheter 10 at its bolus end are substantially balanced.

Rearwardly of the port 35, processed blood is forced out of the third, fourth and fifth ports 36, 37 and 38 at 90° displaced locations around the axis of the tube 11. As a result, processed blood is returned to the patient from five ports at a high rate of flow, but with reaction forces which also tend to be balanced along the tube 11 so as to avoid whipping of any part of the tube in the blood vessel. Flow rates of 500 ml/min. are achievable with little or no vessel trauma.

At the same time that forces exerted by processed blood flow are balanced by the afore-described port arrangement, the configuration of the ports 35–38 contributes greatly to smooth flow and minimal blood corpuscle damage. Because the ports 35–38 are longitudinally elongated and have rounded edges the processed blood under pressure flows smoothly out of them and tends to adhere to the outer surface 29 of the tube body 24 as it flows toward and over the bolus 20.

Processed blood flowing out of the main port 69 is induced by the relationship of the main port to the bullet-shaped nose on the nose section 57 of the bolus body 51 to spiral about the axis of the vein as it travels over the nose. This induced spiraling of processed blood flow, which normally is counter-clockwise about that axis, increases the rate of diffusion of processed blood as it departs the catheter.

Referring now to FIGS. 13–15, a catheter comprising features of another form of the first embodiment of the invention is seen generally at 110. The catheter 110 includes a cylindrical tube 111 preferably fabricated of silicone. The proximal end of the tube 111 has a connector (not shown) attached in a conventional manner. The distal end 115 of the tube 111 has a bolus 120 mounted thereon.

The tube 111 in the catheter 110 comprises a tubular body 124, including a generally cylindrical wall 125 which defines a cylindrical lumen 127 extending through the body, along its entire length. The wall 125 has an inner surface 128 and an outer surface 129.

The bolus 120 in the catheter 110 has a body 151. The body 151 comprises a connector section 155, an elongated flow passage section 156 and a bullet-nose section 157.

The lumen 127 in the tube body 124 communicates with the flow passage section 156 in the bolus body 151. The flow passage section 156 in the body 151 includes an elongated, axially extending passage 166 and a shorter, axially and radially extending passage 167 having a base 168 which curves across the axis of the body 151 to form one end of a main port 169 in the side of the bolus body. The main port 169 is enlarged by forming sides 171 for the radial passage 167 down low enough so that the main port extends circumferentially around about 190° of the body 151. Again, the trailing ends of the sides 171 are inclined at a 45° angle.

Directly opposite the center of the main port 169 the floor 172 of the radial passage 167 is thickened, as at 173, to form a stiffening arch in the bolus 120. The arch 173 begins under the elongated, axially extending passage 166, increases in thickness until it is directly under the port 169, and then decreases in thickness toward the front end of the nose section 157.

The elongated flow passage section 156 of the bolus body 151 also has a second port 185 formed radially through it. The port 185 is circumferentially displaced 180° from the main port 169 around the longitudinal axis of the bolus 120.

The port 185 is formed during molding so as to have a race-track shape longitudinally of the section 156. In a standard 10 French hemodialysis tube assembly, the port 185 is 0.100 inches long and 0.050 inches wide. As seen in FIG. 14 the edge 189 of the race-track shaped port 185 is semi-circular in cross-section. In other words, it is rounded along its entire length.

Directly opposite the second port 185, the wall of the passage section 156 is thickened in an oval pattern to form an elongated dimple 195. At its thickest, the dimple 195 is about 40% thicker than the rest of the wall. The dimple 195 amounts to an oval shaped stiffening arch formed in the wall of the passage section 156 opposite the second port 185, the arch being about two and one-half times as long as the port.

The arch formed by the dimple 195 serves multiple purposes in the catheter 110. It prevents the bolus 120 from buckling at the second port 185. It stiffens the edge 191 of the main port 169 where it emerges from the bolus body 151. It serves to hold the main port 169 away from the vein wall and protect the vein wall from abrasion by the edge 191 of the main port.

The elongated flow passage section 156 of the bolus body 151 also has a third port 198 formed radially through it in the form illustrated. The port 198 is circumferentially displaced 180° from the second port 185 around the longitudinal axis of the bolus 120. In other words, it is axially aligned with the main port 169.

The port 198 is also formed during molding so as to have a race-track shape longitudinally of the section 156. The port 198 is 0.100 inches long and 0.050 inches wide. The edge 199 of the race-track shaped port 198 is semi-circular in cross-section. Thus, it is rounded along its entire length.

Directly opposite the third port 198, the wall of the passage section 156 is thickened in an oval pattern to form an elongated dimple 205. Again, the dimple 205 amounts to an oval shaped stiffening arch formed in the wall of the passage section 156 opposite the section port 198, the arch being about two-and-one-half times as long as the port. The dimple 205 slightly overlaps the dimple 145 longitudinally of the bolus 120 so that they effectively cooperate in stiffening the bolus at the ports 185 and 198.

The arch formed by the dimple 205 serves multiple purposes in the catheter 110. It prevents the bolus 120 from buckling at the third port 198. It also serves to hold the second port 185 away from the vein wall and protect the vein wall from abrasion by the edge 191 of the main port.

This form of bolus 120 may also be used without the third port 198. In such case, whether used as a venous or arterial flow catheter, higher flow rates, better diffusion and less vein damage are still achieved when compared to prior art catheters.

Referring now to FIG. 16, a catheter 110 embodying features of the other form of the first embodiment of the invention is shown in place in the superior vena cava (SVC) of a patient. The catheter 110 has been introduced through the external jugular vein in the patient's neck and fed through that vein into the SVC.

As will be seen, in following this course the catheter bolus 120 has to lead the catheter around what amounts to two 90° bends to get to the SVC. The bends are indicated at A and B. In navigating the bends, the bullet-nosed body 151 of the bolus 120 tends to slide along the surface of the vein wall, without abrading the wall as it passes. As a result, vein wall damage is avoided during insertion; such damage being a common occurrence with conventional catheters.

Referring now to FIG. 17, a hemodialysis catheter comprising one form of a second embodiment of the invention is seen generally at 310. The catheter 310 includes a cylindrical tube 311 which is preferably fabricated from silicone.

The tube 311 extends between a proximal end 314, which may be connected to hemodialysis device, and a distal end 315. As shown in FIG. 17, the proximal end 314 has a conventional connector 316 attached. The tube 311 has a bolus 320 on its distal end 315.

Referring additionally to FIGS. 18–26, the tube 311 comprises a tubular body 324 including a generally cylindrical wall 325. The body 324 is divided by a system 326 which defines two identical D-shaped lumens 327A and 327B extending through the body, along its entire length. The wall 325 has an inner surface 328 and an outer surface 329.

The distal end 15 of the tube 311 joins the bolus 320 at the line 331. Forward of the line 331 the tube body 324 has a necked down end 333 (see FIG. 19) which is seated in a suitably formed socket 334 in the bolus 320 and glued or ultrasonically welded to the bolus.

The tube body 324 has a venous port 335 and an arterial port 337 formed radially through it adjacent the distal end 315 of the tube 311, and longitudinally spaced from each other. The ports 335 and 337 are, in addition to being longitudinally spaced, also displaced 180° from each other circumferentially around the axis of the tube body 324. In compass point terms, the port 335 is at 180° and the port 337 is at 0°/360°. The port 335 communicates with the venous lumen 327B and the port 337 with the arterial lumen 327A.

The ports 335 and 337 are identical to each other. Accordingly, only the port 337 will be described. The port 337 is formed through the tube body wall 325 during molding so as to have a racetrack shape longitudinally of the tube 311. The port 337 is 0.040 inches long and 0.020 inches wide.

The edge 339 of the racetrack shaped port 337 is semi-circular in cross-section, i.e., rounded along its entire length. The wall 325 is 0.040 inches thick where the port 337 is formed. Thus, the radius of the semi-circular edge 339 is 0.020 inches.

The ports 335 and 337 are spaced longitudinally so that their centerlines, seen at the section lines 21—21 and 22—22 in FIG. 18, are 0.175 inches apart. The centerline of the arterial port 335 is, in turn, spaced 0.175 inches from the centerline of the bolus 320 ports, hereinafter described.

Immediately opposite each of the ports 335 and 337 in the tube wall 325, the wall is thickened in an oval pattern to form an elongated dimple. At its thickest, each dimple 345 and 347 is about 40% thicker than the rest of the tube wall 325. The dimple is centered on the corresponding port opposite it. Thus, a stiffening arch is formed in the tube wall 325 opposite each port.

The bolus 320 has a body 351 also preferably formed of silicone. The dimensions of the body 351 will vary with the size of the catheter tube 311 in use, but in the present illustration they are those of the 13.5 French tube.

The bolus body 351 has a tube connector section 355, a flow passage section 356 and a bullet nose section 357. The tube connector section 355 has a septum 358 formed in it. The septum 358 mates, end-to-end, with the septum 326 in the tube body 324, as best seen in FIG. 19. The septum 326 then extends into the flow passage section 356. The septum 358 divides the flow passage section 356 into an upper arterial passage 359A and a lower venous passage 359B.

The lumens 327A and 327B in the tube body 324 communicate with the passages 359A and 359B in the bolus body 351 through the connector section 355, above and below the septum 358. The passage 359B extends to the end 361 of the septum 358 where it enters a radial passage 367 having a base 368 which curves across the axis of the body 351 to form one end of a main outflow or venous port 369 in the body. The outflow port 369 is enlarged circumferentially by forming low sides 371 for the radial passage 367 so that the port 369 extends circumferentially around about 190° of the axis of the body 351.

The passage 359A opens at its inclined (at 45°) leading edge 363, above the septum 358, short of the end 361 of the septum. There, a radial intake or arterial port 366 is formed in the bolus above the level of the septum 358 and extending circumferentially around about 175° of the axis of the body 361. The arterial port 366 and the venous port 369 together form one continuous opening on the side of the bolus body 351 between the connector section 355 and the bullet nose section 357.

Immediately behind the leading edge 363, two segmentally circular supplemental arterial ports 368A and 368B are formed through the side wall of the lumen. The ports 368A and 368B are nominally 0.05 inches in diameter but are flattened along their lower edges where they abut the septum 358.

Directly opposite the center of the combined ports 366 and 369, the floor 372 of the radial passage 367 is thickened, as at 373, to form a stiffening arch in the bolus 320. The arch 373 begins at about the end of the tube body 324, increases in thickness until it is directly under the ports 366 and 369, and then decreases in thickness to the bullet nose section 357.

The port 369 is a venous or outflow port for the venous lumen 327B, as has been pointed out. Outflow is around the end of the septum 358 and forwardly over the bullet nose section 357 of the bolus body 351.

The port 335 is also a venous or outflow port, as has been pointed out. Outflow through the port 335 is directed opposite the catheter axis from that of the port 369, because the port 335 is 180° displaced from the port 369.

The port 366 is an arterial or intake port for the arterial lumen 327A, as has also been pointed out. Intake is above the lumen 358, axially displaced from the outflow of the port 369. Intake also occurs through the ports 368A and 368B and the port 337. The port 337 communicates with the arterial lumen 327A in the tube 311.

Referring now to FIGS. 27–35, a first variation of another form of the second embodiment of dual lumen catheter comprising features of the invention is illustrated generally at 410. The catheter 410 comprises a cylindrical tube 411 having a proximal end 414 and a distal end 415. A bolus 420 is attached to the distal end 415.

The tube 411 is a 13.5 French tube preferably formed of silicone. The tube 411 comprises a tubular body 424 with a generally cylindrical wall 425 having a thickness of 0.040 inches. The body 424 is divided by a septum 426 which defines two identical D-shape lumens 427A and 427B extending through the body along its length. The lumen 427A is an arterial lumen and the lumen 427B is a venous lumen. Each lumen 427A and 427B has a cross-sectional area of 0.005 inches.

The distal end 415 of the dual lumen tube 411 joins the bolus 420 at 431. Here, the tube body 424 has a necked down end 433 which is seated in a suitably formed socket 434 in the bolus 420. The bolus 420 has a body 451 also preferably formed of silicone. The tube 411 and bolus 420 are mated in this fashion after each is formed of raw silicone. The silicone is then cured. When cured, mated portions of the tube 411 and the bolus 420 are effectively welded together.

The bolus body 451 includes a tube connector section 455, a flow passage section 456 and a bullet nose section 457. The bolus body 451 is 1.62 inches long.

Figure 29:
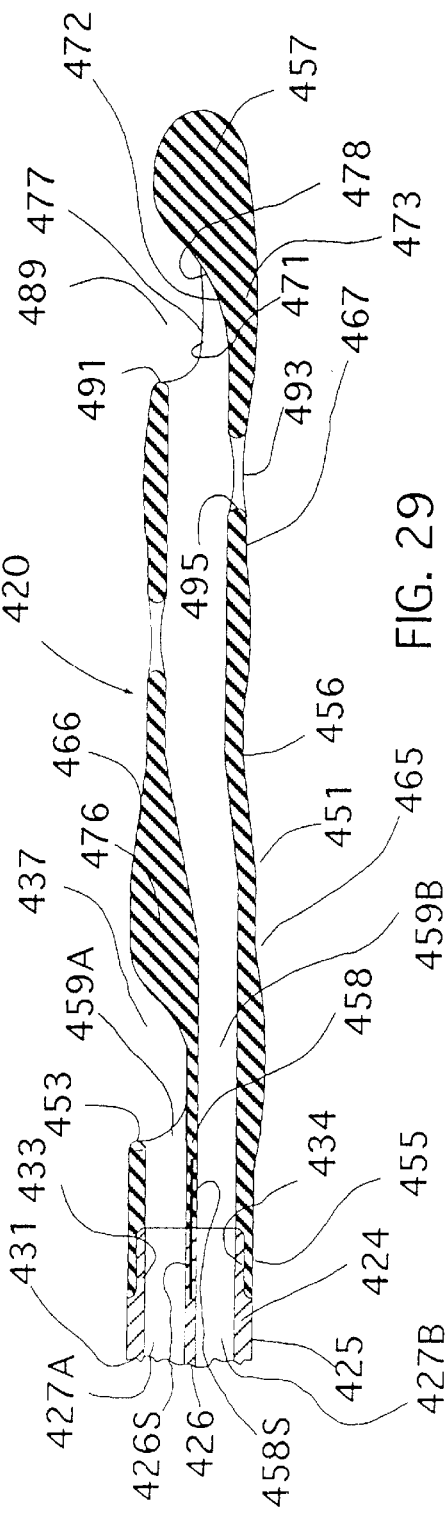
FIG. 29 is a longitudinal sectional view through the bolus end of the catheter seen in FIG. 28.

The tube connector section 455 is a 13.5 French diameter section having a septum 458 formed in it. The septum 458 mates, end-to-end, with the septum 426 in the tube body 426. As best seen in FIGS. 29 and 30, a slit 426S is formed into the end of the septum 426, halfway between its upper and lower surfaces. A corresponding slit 458S is formed into the end of the septum 458. These slits receive a 0.005 inch thick nylon card 452 which aligns the opposed ends of the lumens 426 and 458 so that they will be welded together end-to-end.

The septum 458 forms D-shape upper and lower passages 459A and 459B in the tube connector section 455. Each has a cross-sectional area of 0.005 inches. The upper passage 459A is an arterial passage. The lower passage 459B is a venous passage.

Extending forwardly from the tube connector section 455 is the flow passage section 456 of the bolus body 451. The flow passage section 456 comprises three axially aligned sub-sections, a 13.5 French diameter sub-section 465, a transition sub-section 466 and a 10 French diameter sub-section 467.

In the bolus body 451, the 13.5 French sub-section 465 is 0.400 inches long, the transition sub-section 466 is 0.175 inches long and the 10 French sub-section 467 is 0.487 inches long. The nominal O.D. of the 13.5 French sub-section 465 is 0.180 inches while the nominal O.D. of the 10 French sub-section 467 is 0.136 inches.

The 13.5 French sub-section 465 contains continuations of upper arterial passage 459A and lower venous passage 459B. The lower venous passage 459B has a uniformly dimensional D-shape, as seen in FIG. 30, for 0.300 inches of its length. The cross-sectional area is about 0.005 in$^2$. Then the passage 459B begins to change in shape and increase slightly in cross-sectional area until it has a circular cross-section of about 0.006 in$^2$.

The upper arterial passage 459A in the 13.5 French sub-section 465 extends forwardly above the septum 458 to the radial arterial port 437. The radial arterial port 437 is 0.265 inches long at the outer surface of the bolus body 451 and extends circumferentially around the body's axis from the upper surface of the septum 458 on one side of the tube to the upper surface of the septum in its other side. As such, the port 437 has a plan cross-sectional area for venous flow of 0.048 inches, as seen in FIG. 31.

The leading edge 473 of the bolus body 451 above the passage 459A (which forms the trailing edge of the port 437) is rounded along its entire length down to the septum, as seen in FIG. 29. The thickness of the 13.5 French body 451 at this edge 473 is 0.026 inches, so the radius of the rounded edges is 0.013 inches.

Forward of the arterial port 437 in the 13.5 French sub-section 465 of the bolus body 451 this sub-section becomes solid, as at 476. In effect, the septum 458 melds into this solid portion 476 of the bolus body 451.

The transition sub-section 466 of the bolus body 441 is externally frusto-conical whereby the bolus body is reduced in size from 13.5 French to 10 French. The aforedescribed solid portion 476 of the 13.5 French sub-section 465 melds into the frusto-conical transition sub-section 466.

Meanwhile, inside the transition sub-section 466, the venous passage 459B changes from a distorted D-shape, where the transition sub-section 466 begins, to a round or cylindrical shape where it ends. The bolus body 451 at this point has the cross-sectional shape and size seen in FIG. 33. It has an internal cross-sectional area of 0.006 in$^2$, the size of a 10 French tube.

The 10 French sub-section 467 of the flow passage section 456 in the bolus body 451 then continues forwardly to the bullet nose section 457 of the bolus body 451. The passage 459B enters a radial passage 447 having a base 478 which curves across the body 451 to form the front end of a main outflow or venous port 489 in the body. The port 489 extends circumferentially around 190° of the body 451 to its side edges 471.

The port 489 is 0.240 inches long from its trailing edge 491 to the nose section 457 of the bolus body 451. The edge 491 rounded along its entire length, as are the side edges 471, which are continuations of the edge 491. As seen in FIG. 34, the port 489 has an expanded plan area of 0.058 in$^2$.

Directly opposite the center of the port 489, the floor 472 of the radial passage 467 is thickened to form a stiffening arch 473 in the bolus. The arch 473 begins at a second venous port 493 in the bolus body 451, increases in thickness until it is directly under the port 489, and then decreases in thickness to where the passage section 456 joins the bullet nose section 457.

The second venous port 493 has a racetrack shape, as seen in FIG. 35. It is 0.100 inches long and 0.050 inches wide, with a plan cross sectional area of 0.004 in$^2$. The edge 494 of the port 493 is curved in cross-section along its entire length. The radius of the curve is 0.0125 inches.

The centerline of the second venous port 493 is axially displaced 0.175 inches from the centerline of the main venous port 489. The second port 493 is circumferentially displaced 180° around the bolus body 451 from the main venous port 489.

A third venous port 501 is formed in the passage sub-section 466 displaced axially 0.175 inches from the second port 493. The port 501 is identical in configuration and size to the port 493. It is circumferentially displaced 180° from the port 493 and, as such, is axially aligned with the main venous port 489.

The venous ports 493 and 501 have stiffening arches 495 and 505, respectively, formed in the bolus body 451 opposite them. The arches 495 and 505 overlap slightly longitudinally of the bolus 420.

Referring now to FIG. 36, a catheter 410 is shown there in place in the superior vena cava (SVC) of a patient. The catheter 410 has been introduced through the external jugular vein in the patient's neck and fed through that vein into the SVC.

As will be seen, in following this course the catheter bolus 420 has to lead the catheter 410 around what amounts to two 90° bends in the jugular vein and the SVC. The bends are indicated at A and B. In navigating the bends, the bullet-nosed body 451 of the bolus 420 tends to slide along the surface of the vein wall, without abrading the wall as it passes. As a result, vein wall damage is avoided during insertion; such damage being a common occurrence with conventional catheters.

Although FIG. 36 illustrates insertion of a catheter 410, it should be understood that this form of the second embodiment catheter is used here merely as an example. FIG. 36 could as readily have illustrated placement of a catheter 310 comprising features of the first form of the second embodiment.

Regarding the catheter 410 specifically, however, it has particularly advantageous features. Because the leading half (10 French sub-section 467 and nose section 457) is only 75% of the diameter of the trailing half (13.5 French and transition sub-sections 465 and 466), inserting the catheter 410 into a patient's vein is made easier. The smaller diameter of the leading half of the bolus 420 also makes it more flexible, permitting the catheter 410 to travel around bends in the receiving vein more easily.

When it is in place in a patient, the catheter 410 also has other advantages. The venous ports 489, 493 and 501 are held away from the vein wall by the larger diameter 13.5 French sub-section 465. More blood is available around the venous ports 489, 493 and 501 than around the arterial port 437, making it less likely that blood will be pulled directly away from the venous ports by the arterial port 437 in the larger diameter 13.5 French sub-section 465.

Now referring to FIGS. 37–40, a second variation of the other form of the second embodiment of dual lumen catheter is illustrated at 610. The catheter 610 includes the bolus shown at 620. The bolus 620 has a body 651 also preferably formed of silicone. The bolus 620 is mated to a catheter tube 611 in the same manner as the bolus 420.

The bolus body 651 is 1.436 inches long, i.e., about 10% shorter than the bolus body 451. The body 651 includes a tube connector section 655, a flow passage section 656 and a bullet nose section 657.

The tube connector section 655 is a 13.5 French diameter section which has a septum 658 formed in it. The septum 658 mates, end-to-end, with the tube body septum.

The septum 658 forms D-shape upper and lower passages 659A and 659B in the tube connector section 655. Each has a cross-sectional area of 0.005 inches. The upper passage 659A is an arterial passage. The lower passage 659B is a venous passage.

Extending forwardly from the tube connector section 655 is the flow passage section 656 of the bolus body 651. The flow passage section 656 comprises three axially aligned sub-sections, a 13.5 French diameter sub-section 665, a transition sub-section 666 and a 10 French diameter sub-section 667. The nominal O.D. of the 13.5 French subsection 665 is 0.180 inches while the nominal O.D. of the 10 French sub-section 667 is 0.136 inches.

The 13.5 French sub-section 665 contains continuations of upper arterial passage 659A and lower venous passage 659B. The lower venous passage 659B has a uniformly dimensioned D-shape, as seen in FIG. 39, for 0.268 inches of its length. The cross-sectional area is about 0.005 in$^2$. Then the passage 659B begins to change in shape and increase slightly in cross-sectional area, becoming circular with an area of about 0.006 in$^2$.

The upper arterial passage 659A in the 13.5 French sub-section 665 extends forwardly above the septum 658 to the radial arterial port 637. The radial arterial port 637 is 0.255 inches long at the outer surface of the bolus body 651 and extends circumferentially around the body's axis from the upper surface of the septum 658 on one side of the tube to the upper surface of the septum in its other side.

The leading edge 673 of the bolus body 651 above the passage 659A (which forms the trailing edge of the port 637) is rounded along its entire length down to the septum 658. As seen in FIG. 39, this edge 673 is also inclined downwardly at an angle of 45° to where it meets the septum 658.

Forward of the arterial port 637 in the 13.5 French sub-section 665 of the bolus body 651 this sub-section becomes solid, as at 676. The septum 658 melds into this solid portion 676 of the bolus body 651.

The transition sub-section 666 of the bolus body 641 is generally frusto-conical whereby the bolus body is reduced in size from 13.5 French to 10 French. The aforedescribed solid portion 676 of the 13.5 French sub-section 665 melds into the frusto-conical transition sub-section 666.

Meanwhile, inside the transition sub-section 666, the venous passage 659B changes from a distorted D-shape, where the transition sub-section 666 begins, to a round or cylindrical shape where it ends. Here it has an internal cross-sectional area of 0.006 in$^2$, the size of a 10 French tube.

The 10 French sub-section 667 of the flow passage section 656 in the bolus body 651 then continues forwardly to the bullet nose section 657 of the bolus body 651. The passage 659B enters a radial passage 647 having a base 678 which curves across the body 651 to form the front end of a main outflow or venous port 689 in the body. The port 689 extends circumferentially around 190° of the body 651 to its side edges 671.

The port 689 is 0.240 inches long from its trailing edge 691 to the nose section 657 of the bolus body 651. The edge 691 is rounded along its entire length, as are the side edges 671, which are continuations of the edge 691. As seen in FIG. 39, the edge 691 is also inclined at an angle of 45° to where it meets the septum 658.

Directly opposite the center of the port 689, the floor 672 of the radial passage 667 is thickened to form a stiffening arch 673 in the bolus. The arch 673 begins at a second venous port 693 in the bolus body 651, increases in thickness until it is directly under the port 689, and then decreases in thickness to where the passage section 656 joins the bullet nose section 657.

The second venous port 693 has a racetrack shape. It is 0.100 inches long and 0.050 inches wide, with a plan cross sectional area of 0.004 in$^2$. The edge 694 of the port 693 is curved in cross-section along its entire length.

The centerline of the second venous port 693 is axially displaced about 0.275 inches from the centerline of the main venous port 689. The second port 693 is circumferentially displaced 180° around the bolus body 651 from the main venous port 689.

A third venous port 701 is formed in the passage sub-section 666 displaced axially about 0.210 inches from the second port 693. The port 701 is identical in configuration and size to the port 693. It is circumferentially displaced 180° from the port 693 and, as such, is axially aligned with the main venous port 689.

It will be noted that in this form of bolus, the second venous port 693 again has a stiffening arch 695 opposite it. However, the third venous port 701 does not. In this shortened bolus 620, the stiffening element opposite the third port can be eliminated because the transition sub-section 666 of the bolus body 651 extends underneath it and stiffens the bolus 620 there.

With regard to this transition sub-section 666, it is conically shaped beneath the venous lumen 627B. It is actually rounded or bulbous shaped above the venous lumen 627B.

The bolus 620 also differs from the bolus 420 in several other aspects. The bolus 620 has second and third arterial ports 638L and 638R immediately downstream (in the direction of arterial flow) of the arterial port 637. The ports 638L and 638R are segmentially circular in shape and have an inside diameter (in their circular portions) at their innermost edges of 0.50 inches. The edges 639 are, again, arcuate in cross-section.

As best seen in FIGS. 39 and 40, the ports 638L and 638R are slightly truncated circles in shape, the truncation being along lower edge portions 639L and 639R defined by the septum 658. Each port 638L and 638R has a cross-sectional area of approximately 0.002 in$^2$.

The arterial port 637 has a cross-sectional area of 0.006 in$^2$. The two ports 638L and 638R thus have a combined arterial flow cross-section which is two-thirds of that of the main arterial port 637. They function as an intake for two-thirds of the arterial flow, leaving one-third for flow through port 637.

The result is a highly effective arterial port system with virtually no danger of occlusion. The use of two ports 638L and 638R opposite each other, immediately adjacent the septum 658, in combination with the main arterial port 637, produces a lower velocity inflow at each port. This lower velocity further prevents the vein wall from being sucked against any of the arterial ports. Because each port 638L and 638R extends downwardly to the septum 658, there is also no dead space corner below the port and above the septum.

The bolus 620 is shorter than the bolus 420 previously described. This is achieved by shortening the transition sub-section 666 in the passage section of the bolus body 651. The venous and arterial ports 701 and 637 are closer together (axially) as a result. Thus, the shorter bolus 620 results in both venous and arterial ports being effective in the same vein or heart area.

The shorter bolus 620 reduces further the chance of kinking in the bolus. Although the bolus 620 is shorter, the full round 10 French section of the bolus remains long enough so that all venous ports are fed from a full round portion of the venous lumen 659B.

The bulbous shape of the transition sub-section 666 of the bolus 620 also has another advantage. This shape results in a smoother transition between 13.5 French and 10 French diameters and less irritation to vein walls.

As also seen in FIG. 40, if the vein wall does somehow press against the bolus body 651 over the top of the arterial port 637, openings left on the sides of this port still approximate the size of the D-shaped arterial lumen 659A in cross-section. Therefore, sucking of the vein wall further into the port 637 is rendered additionally unlikely.

Referring now to FIGS. 41–47, a third variation of this form of dual lumen catheter comprising features of the invention is illustrated generally at 810. The catheter 810 comprises a cylindrical tube 811 having a proximal end (not shown) and a distal end 815. A bolus 820 is attached to the distal end 815.

The tube 811 is a 13.5 French tube formed of silicone. The tube 811 comprises a tubular body 824 with a generally cylindrical wall 825 having a thickness of 0.028 inches. The body is divided by a septum 826 which defines two identical D-shaped lumens 827A and 827B extending through the body along its length. The lumen 827A is normally the arterial lumen and the lumen 827B is normally the venous lumen. Each lumen 827A and 827B has a cross-sectional area of about 0.005 in$^2$.

The distal end 815 of the dual lumen tube 811 joins the bolus 820 at 831. Here, the tube body 824 has a necked down end 833 which is seated in a suitably formed socket 834 in the bolus 820. The bolus 820 has a body 851 also formed of silicone. The tube 811 and the bolus 820 are mated in this fashion after each is formed of raw silicone. The silicone is then cured. When cured, mated portions of the tube 811 and the bolus 820 are effectively welded together. The tube 811 and the bolus 820 can also be connected in a more conventional manner, by using silicone glue commonly referred to as RTV glue, for example.

The bolus body 811 is 1.096 inches long. The body 851 includes a tube connector section 855, a flow passage section 856 and a bullet nose section 857.

The tube connector section 855 is a 13.5 French diameter section that is 0.091 inches long and has a septum 858 formed in it. The septum 858 mates, end-to-end with the septum 826 in the tube body. As best seen in FIG. 44, a slit 826S is formed into the end of the septum 858. These slits receive a 0.005 inch thick nylon card 852 which aligns the opposed ends of the lumens 826 and 858 so that they will bond together.

The septum 858 forms D-shaped upper and lower passages 859A and 859B in the tube connector section 855. Each has a cross-sectional area of approximately 0.005 in$^2$. The upper passage 859A is normally the arterial passage. The lower passage 859B is normally the venous passage.

Extending forwardly from the tube connector section 855 is the flow passage section 856 of the bolus body 851. The flow passage section 856 is 1.099 inches long and comprises three axially aligned sub-sections, a 13.5 French sub-section 865, a transition sub-section 866 and a 10 French sub-section 867.

The 13.5 French sub-section 865 is 0.268 inches long. The transition sub-section 866 is 0.316 inches long. The 10 French sub-section is 0.421 inches long. The nominal O.D. of the 13.5 French subsection is 0.180 inches while the nominal O.D. of the 10 French sub-section 867 is 0.136 inches.

The 13.5 French sub-section 865 contains continuations of upper arterial passage 859A and lower venous passage 859B. The lower venous passage 859B has a uniformly dimensional D-shape, as seen in FIG. 14, for 0.268 inches of its length. The cross sectional area is about 0.005 in$^2$. Then the passage 859B begins to change in shape and increase slightly in cross-sectional area, and gradually becoming a full circular shape with a cross-sectional area of about 0.006 in$^2$. During this gradual transition from a D-shape to a full circular shape the cross-sectional area is always 0.005 in$^2$ or greater.

The upper arterial passage 850A in the 13.5 French sub-section 865 extends forwardly above the septum 858 to the radial main arterial port 837. The radial arterial port 837 is 0.308 inches long at the outer surface of the bolus body 851 and extends circumferentially around the body's axis from the upper surface of the septum 858 on one side of the tube to the upper surface of the septum in its other side. As such, the port 837 has a cross-sectional area for flow of approximately 0.60 in$^2$. The leading edge 873 of the bolus body 851 above the passage 859A, which forms the trailing edge of the port 837, is rounded along its entire length down to the septum 858.

Forward of the arterial port 837 in the 13.5 French sub-section 865 of the bolus body 851, this sub-section becomes solid, as at 876. In effect, the septum 858 melds into this solid portion 876 of the bolus body 851.

The transition sub-section 866 of the bolus body 851 is externally frusto-conical whereby the bolus body is reduced in size from 13.5 French to 10 French. The aforedescribed solid portion 876 of the 13.5 French sub-section 865 melds into the frusto-conical transition sub-section 866.

Meanwhile, inside the transition sub-section 866, the venous passage 859B changes from a distorted D-shape, where the sub-section 866 begins, to a round or cylindrical shape where it ends. The 10 French sub-section 867 of the flow passage section 856 in the bolus body 851 then continues forwardly to the bullet nose section 857 of the bolus body 851. The passage 859B enters a radial passage 877 having a base 878 which curves across the body 851 to form the front end of a main outflow or venous port 859 in the body. The port 889 extends circumferentially around 190° of the body 851 to its side edges 871.

The port 889 is displaced 180° from the arterial port 837 around the axis of the axis of the bolus body 851. The port 889 is 0.308 inches long from its trailing edge 891 to the nose section 857 of the bolus body 851. The edge 891 is rounded along its entire length, as are the side edges 871, which are continuations of the edge 891. The port 889 has an expanded plan area of 0.044 in$^2$.

Directly opposite the center of the port 889, the floor 872 of the radial passage 877 is thickened to form a stiffening arch 873 in the bolus. The arch 873 begins at the 13.5 French portion of the bolus body and extends to where the passage section 856 joins the bullet nose section 857.

In this variation, the bullet nose section 857 and the forward end of the passage section 856 are not only 10 French in size but are offset downwardly from the center line of the tube 811, as best seen in FIGS. 44 and 45. This places the venous port 889 further from the arterial port 837 than in previously described forms of the dual lumen bolus. It is also contemplated, however, that the nose section 857 might be on the center line of the tube 811, as seen in FIGS. 46 and 47, and still retain most of the advantages which flow from the bolus 820 configuration shown in FIGS. 41–45.

While preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

What is claimed is:

1. A blood vessel catheter, comprising:
   a) an elongated tube including a body having a proximal end and a distal end;
   b) said body including a generally cylindrical wall enclosing a lumen;

c) a longitudinally elongated bolus on said distal end of said tube body, said bolus including a bolus body having a tube connector section connected to said tube body, a passage section and a nose section, said nose section forming a closed front end on said bolus body;

d) said passage section containing a passage extending to a main port in the side of said passage section;

e) a radially extending second port in one of said tube body wall and said bolus passage section, said second port being displaced approximately 180° around said catheter from said main port; and f) a thickened portion is formed opposite said second port in a corresponding tube body wall or passage section; and g) said thickened portion being elongated longitudinally of said catheter and comprising a stiffening arch.

2. The blood vessel catheter of claim 1 further characterized in that:

a) said main port extends circumferentially around more than 180° of the circumference of said bolus.

3. A blood vessel catheter, comprising:

a) an elongated tube including a body having a proximal end and a distal end;

b) said body including a generally cylindrical wall having an inner surface and an outer surface;

c) a lumen inside said inner surface of said wall, said lumen extending through said body from said proximal end to said distal end;

d) a longitudinally elongated bolus on said distal end of said body, said bolus having a nose section and a passage section, said passage section containing a passage extending to a main port in the side of said passage section;

e) a radially extending second port in one of said tube body wall and said bolus passage section;

f) said second port being displaced approximately 180° around said catheter from said main port; and g) a radially extending third port in one of said tube body wall and said bolus passage section;

h) said third port being approximately axially aligned with said main port and displaced approximately 180° around said catheter from said second port; and i) a thickened portion formed opposite each of said second and third ports in one of said tube body wall and said passage section;

j) each of said thickened portions being elongated longitudinally of said catheter and comprising a stiffening arch.

4. The catheter of claim 3 further characterized in that:

a) said second and third ports are longitudinally elongated so as to have a racetrack configuration.

5. The catheter of claim 4 further characterized in that:

a) said second and third ports each have a semi-circular side edge extending entirely around the port.

6. The catheter of claim 4 further characterized in that:

a) said nose section has a generally bullet-shaped leading end without an opening in it.

7. A hemodialysis catheter, comprising:

a) an elongated catheter tube including a tube body having a proximal end and a distal end;

b) said body including a generally cylindrical wall enclosing a venous lumen and an arterial lumen separated by a septum;

c) a longitudinally elongated bolus on said distal end of said tube body, said bolus including a bolus body having a tube connector section connected to said tube body, a passage section and a nose section, said nose section forming a closed front end on said bolus body;

d) said passage section containing a venous passage and an arterial passage, said venous passage communicating with said venous lumen and said arterial passage with said arterial lumen;

e) a main venous port formed in one side of said bolus body adjacent said nose section and communicating directly with said venous passage;

f) a second venous port formed in at least one of said bolus body and said tube body, said second venous port being circumferentially displaced about 180° from said main venous port around the axis of said catheter and communicating directly with at least one of said venous passage and said venous lumen; and g) an arterial port formed in at least one of said tube body and said bolus body, said arterial port communicating directly with at least one of said arterial passage and said arterial lumen;

h) both said tube body and said bolus body being formed of silicone; and i) directly opposite each of said ports, a thickened portion forms a stiffening arch.

8. The catheter of claim 7 further characterized in that:

a) said main venous port and said second venous port both directly communicate with said venous passage; and b) said arterial port directly communicates with said arterial passage.

9. The catheter of claim 8 further characterized in that:

a) said arterial port extends around said tube body to opposite edges which are substantially at the level of said septum.

10. The catheter of claim 7 further characterized in that:

a) said nose section includes a bullet nose which forms said closed front end.

11. The catheter of claim 7 further characterized in that:

a) said arterial port comprises a main arterial port formed in one side of said bolus body; and b) said tube body has a second arterial port formed therein.

12. A hemodialysis catheter, comprising:

a) an elongated catheter tube including a tube body having a proximal end and a distal end;

b) said body including a generally cylindrical wall enclosing a venous lumen and an arterial lumen separated by a septum;

c) a longitudinally elongated bolus on said distal end of said tube body, said bolus including a bolus body having a tube connector section connected to said tube body, a flow passage section and a nose section, said nose section forming a closed front end on said bolus body;

d) said flow passage section containing a venous passage and an arterial passage, said venous passage communicating with said venous lumen and said arterial passage with said arterial lumen;

e) a venous port formed in one side of said bolus body adjacent said nose section and communicating directly with said venous passage; and f) an arterial port formed in one side of said bolus body, said arterial port communicating directly with said arterial passage;

g) said bolus body having a relatively larger diameter where said arterial port is located and a relatively smaller diameter where said venous port is located.

13. The catheter of claim 12 further characterized in that:
a) said nose section includes a bullet nose which forms said closed front end.

14. The catheter of claim 12 further characterized in that:
a) said bolus body includes a tapered sub-section between a larger diameter sub-section and a smaller diameter sub-section.

15. A bolus for a hemodialysis catheter, comprising:
a) a longitudinally elongated bolus body having a tube connector section connected to said tube body, a flow passage section and a nose section;
b) said flow passage section containing a venous passage and an arterial passage;
c) a venous port formed in said flow passage section adjacent said nose section and communicating directly with said venous passage; and
d) an arterial port formed in said flow passage section, said arterial port communicating directly with said arterial passage;
e) said bolus body having a relatively larger diameter where said arterial port is located and a relatively smaller diameter where said venous port is located.

16. The bolus of claim 15 further characterized in that:
a) said flow passage section includes a tapered sub-section between a larger diameter sub-section and a smaller diameter sub-section of said flow passage section.

17. The bolus of claim 16 further characterized by and including:
a) another venous port formed in said smaller diameter sub-section of said flow passage section.

18. The bolus of claim 17 further characterized by and including:
a) a further venous port formed in said smaller diameter sub-section of said flow passage section.

19. The bolus of claim 18 further characterized in that:
a) each of said venous ports is elongated longitudinally of said bolus.

20. The catheter of claim 16 further characterized in that:
a) said nose section includes a bullet nose which forms a closed front end on said bolus.

21. The bolus of claim 15 further characterized in that:
a) said venous passage includes a substantially D-shaped passage portion adjacent said connector section and a substantially cylindrical passage portion adjacent said nose section.

22. The bolus of claim 21 further characterized in that:
a) The cross-sectional dimension of said substantially cylindrical passage portion is larger than the cross-sectional dimension of said substantially D-shaped passage portion.

* * * * *